United States Patent
Sul et al.

(10) Patent No.: US 10,180,407 B2
(45) Date of Patent: Jan. 15, 2019

(54) CAPACITOR TYPE HUMIDITY SENSOR

(71) Applicant: Haechitech Corporation, Cheongju-si (KR)

(72) Inventors: Jung Hoon Sul, Seoul (KR); Tak Jun Oh, Seoul (KR)

(73) Assignee: Haechitech Corporation, Cheongju-si (KR)

( * ) Notice: Subject to any disclaimer, the term of this patent is extended or adjusted under 35 U.S.C. 154(b) by 120 days.

(21) Appl. No.: 14/677,553

(22) Filed: Apr. 2, 2015

(65) Prior Publication Data

US 2015/0369768 A1    Dec. 24, 2015

(30) Foreign Application Priority Data

Jun. 18, 2014 (KR) .................. 10-2014-0074013

(51) Int. Cl.
*G01N 27/22* (2006.01)

(52) U.S. Cl.
CPC .................. *G01N 27/223* (2013.01)

(58) Field of Classification Search
None
See application file for complete search history.

(56) References Cited

U.S. PATENT DOCUMENTS

| | | | | |
|---|---|---|---|---|
| 5,235,267 A | * | 8/1993 | Schoneberg | G01D 5/24 324/678 |
| 5,525,910 A | * | 6/1996 | Uhling | G01R 1/06772 219/121.69 |
| 6,731,121 B1 | * | 5/2004 | Hsu | G01D 5/24 324/678 |
| 6,903,558 B1 | * | 6/2005 | Blom | G01R 27/02 324/712 |
| 9,157,937 B2 | * | 10/2015 | Nervegna | G01N 27/26 |
| 2004/0182153 A1 | | 9/2004 | Hamamoto | |
| 2006/0186901 A1 | * | 8/2006 | Itakura | G01N 27/223 324/689 |

(Continued)

*Primary Examiner* — Jermele M Hollington
*Assistant Examiner* — Douglas X Rodriguez
(74) *Attorney, Agent, or Firm* — NSIP Law (57) ABSTRACT

A capacitor type humidity sensor is provided, where a reference capacitor ($C_R$) is provided as an MIM (metal insulator metal) capacitor or a PIP (polysilicon insulator polysilicon) capacitor. The MIM capacitor or PIP capacitor is aligned in array structure to enable the trimming. The capacitor type humidity sensor includes a sensing capacitor ($C_S$) connected between negative (−) drive voltage terminal (−$V_{DRV}$) and an inverting terminal (−) of an operational amplifier, and a reference capacitor ($C_R$) connected between positive (+) drive voltage terminal (+$V_{DRV}$) and an output node (a) of the sensing capacitor ($C_S$), wherein the sensing capacitor ($C_S$) is configured to trim the reference capacitor ($C_R$).

15 Claims, 4 Drawing Sheets

(56) References Cited

U.S. PATENT DOCUMENTS

| | | | |
|---|---|---|---|
| 2012/0007215 A1* | 1/2012 | Darabi | H01L 23/5223 257/532 |
| 2014/0184435 A1* | 7/2014 | Wang | H03M 1/38 341/161 |
| 2015/0083896 A1* | 3/2015 | Xu | G01J 1/18 250/214 A |
| 2015/0253372 A1* | 9/2015 | Watanabe | G01N 27/223 324/538 |

* cited by examiner

CAPACITOR TYPE HUMIDITY SENSOR

CROSS-REFERENCE TO RELATED APPLICATIONS

This application claims the benefit under 35 USC 119(a) of Korean Patent Application No. 10-2014-0074013 filed on Jun. 18, 2014, in the Korean Intellectual Property Office, the entire disclosure of which is incorporated herein by reference for all purposes.

BACKGROUND

1. Field

The following description relates to a capacitor type humidity sensor. An MIM (Metal-Insulator-Metal) capacitor or a PIP (Polysilicon-Insulator-Polysilicon) capacitor is used as a reference capacitor ($C_R$) to enable trimming.

2. Description of Related Art

A humidity sensor is configured to detect a change in humidity based on an electrical signal, and recently humidity sensors have been embedded in a smart device, such as a smart phone. A humidity sensor recognizes ambient humidity and can be used to visually check the comfort of users.

A humidity sensor optimized for the smart device measures humidity by measuring a change in electrical properties of humidity sensitive materials. The electrical properties include resistance, capacitance, and resonant frequency. A resistive humidity sensor has variable electrical resistance and a capacitor type humidity sensor has variable capacitance according to the humidity.

The capacitor type humidity sensor exhibits long-term reliability and linear property of sensor as compared to the resistive humidity sensor. Thus, the capacitor type humidity sensors are generally chosen for products requiring a high degree of precision and are applicable to a very broad range of products.

The capacitor type humidity sensor is manufactured in capacitor form in which a humidity sensitive polymer such as polyimide, which exhibits variable dielectricity when it absorbs moisture, is used as a dielectric material.

The typical capacitor type humidity sensor consists of a sensing capacitor and a reference capacitor. The capacitance value of sensing capacitor changes in accordance with the humidity and that the capacitance value of reference capacitance is maintained as being constant. A size of the reference capacitor is the same as that of the sensing capacitor in order to remove offsets of sensing capacitor, and the reference capacitor is aligned adjacent to the sensing capacitor.

Figure 1:
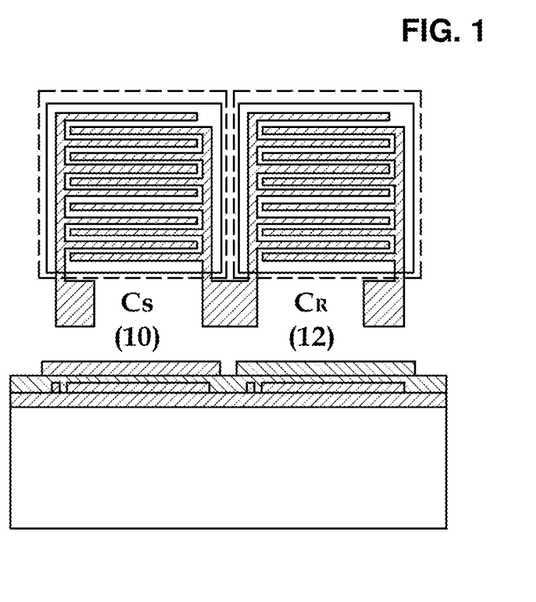
FIG. 1 is a diagram illustrating an example of a typical humidity sensor.

In the example illustrated in FIG. 1, the size of the sensing capacitor ($C_s$) 10 and the size of the reference capacitor ($C_r$) 12 are the same. The sensing capacitor and the reference capacitor are aligned adjacent to each other.

Despite the above-discussed structure and the size of the sensing capacitor ($C_s$) 10 and the reference capacitor ($C_r$) 12, there may be offset differences due to process variation and property differences due to moist-permeable material. As a result, the offset is not substantially removed and removing the offset of the sensing capacitor (Cs) is difficult. In other words, humidity cannot be detected accurately and errors occur.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The present disclosure provides various examples of a capacitor type humidity sensor in which an MIM (Metal-Insulator-Metal) capacitor or a PIP (Polysilicon-Insulator-Polysilicon) capacitor is used as a reference capacitor ($C_R$).

The present disclosure provides various examples where offset differences relative to a sensing capacitor ($C_s$) are removed by performing the trimming with respect to the MIM capacitor or PIP capacitor in array structure. Further, a humidity sensor of relatively small size is provided The present disclosure provides a feedback capacitor ($C_F$) as an MIM capacitor or a PIP capacitor to improve degree of precision by trimming.

In one general aspect there is provided a capacitor type humidity sensor including a sensing capacitor ($C_s$) connected between negative (−) drive voltage terminal (−$V_{DRV}$) and an inverting terminal (−) of an operational amplifier, and a reference capacitor ($C_R$) connected between positive (+) drive voltage terminal (+$V_{DRV}$) and an output node (a) of the sensing capacitor ($C_s$). The sensor is configured to trim the reference capacitor ($C_R$).

The reference capacitor ($C_R$) may include one or more MIM (metal insulator metal) capacitor or PIP (polysilicon insulator polysilicon) capacitor arranged in an array.

Each MIM capacitor or PIP capacitor of the array may have the same value or have a power of 2.

The capacitor type humidity sensor may include a feedback capacitor ($C_F$) connected between the inverting terminal (−) of the operational amplifier and the output terminal ($V_{MEAS}$), wherein the feedback capacitor ($C_F$) comprises one or more MIM (metal insulator metal) capacitor or PIP (polysilicon insulator polysilicon) capacitor configured in an array structure.

The capacitor type humidity sensor may include a reset switch connected between the inverting terminal (−) of the operational amplifier and the output terminal ($V_{MEAS}$) and the reset switch being configured to reset the feedback capacitor ($C_F$).

A gain may be adjusted by applying a gain trimming signal (GAIN_TRIM) to the feedback capacitor ($C_F$).

A non-inverting terminal (+) of the operational amplifier may be connected to the AC ground.

A duty cycle of a voltage +$V_D$ inputted at the positive (+) drive voltage terminal (+$V_{DRV}$) may be different than a duty cycle of a voltage −$V_D$ inputted at the − drive voltage terminal (−$V_{DRV}$) and the duty cycle of the voltage −$V_D$ may be longer than the duty cycle of the voltage +$V_D$.

The capacitor type humidity sensor may include a switch connected to the each MIM capacitor or the PIP capacitor of the array, and the switch being configured to selectively apply a reference trimming signal (REF_TRIM).

A number of the MIM capacitor or a number of the PIP capacitor of the array is determined based on a size and performance of the capacitor type humidity sensor.

In another general aspect there is provided a capacitor type humidity sensor including a first reference capacitor ($C_R$) connected to an inverting terminal (−) of an operational amplifier, and a second reference capacitor ($C_R$) connected to a non-inverting terminal (+) of an operational amplifier, wherein the first and second reference capacitors comprises one or more MIM (metal insulator metal) capacitor or PIP (polysilicon insulator polysilicon) capacitor arranged in an array structure and the first and second reference capacitors being mirror structure of each other.

A trimming signal (REF_TRIM) may be applied to the first and second reference capacitors ($C_R$).

A first feedback capacitors ($C_F$) may be connected between the inverting terminal (−) and output terminal ($V_{MEAS+}$) of the operational amplifier, and a second feedback capacitors ($C_F$) may be connected between the non-inverting terminal (+) and output terminal ($V_{MEAS-}$) of the operational amplifier, wherein the first and second feedback capacitors may comprise one or more MIM (metal insulator metal) capacitor or PIP (polysilicon insulator polysilicon) capacitor configured in an array structure.

A gain may be adjusted by applying a gain trimming signal (GAIN_TRIM) to the first and second feedback capacitors ($C_F$).

The capacitor type humidity sensor may include a sensing capacitor ($C_s$) connected between the inverting terminal (−) and the non-inverting terminal (+) of the operational amplifier and between positive (+) drive voltage terminal (+$V_{DRV}$) and negative (−) drive voltage terminal (−$V_{DRV}$).

In another general aspect this is provided, a capacitor type humidity sensor including The reference capacitor is an MIM capacitor or a PIP capacitor in array structure and in mirror structure.

A reference capacitor of a capacitor type humidity sensor ($C_R$) of the examples described in the present disclosure is manufactured in an MIM (metal insulator metal) capacitor or a PIP (polysilicon insulator polysilicon) capacitor. Thus, it is possible to manufacture a capacitor type humidity sensor of relatively small size in comparison with the typical capacitor humidity sensor having the same capacitance.

A reference capacitor of a capacitor type humidity sensor ($C_R$) of the examples described in the present disclosure can dispose an MIM capacitor or a PIP capacitor at an arbitrary position under the sensing capacitor ($C_S$). An alteration of designing is easy.

In the present examples, the reference capacitor ($C_R$) is realized as one or more MIM capacitors or PIP capacitors to enable the trimming. Hence, it is possible to reduce or remove offsets of the sensing capacitor ($C_S$). Moreover, a feedback capacitor ($C_F$) can be embodied as an MIM capacitor or a PIP capacitor to enable the trimming. Therefore, the degree of precision regarding the humidity sensor can be improved.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The present examples describe a capacitor type humidity sensor in which a reference capacitor ($C_R$) and a feedback capacitor ($C_F$) are provided as MIM capacitor or a PIP capacitor to enable the trimming. Accordingly, offset values of the sensing capacitor ($C_S$) are reduced or removed and a chip size is reduced.

Figure 2:
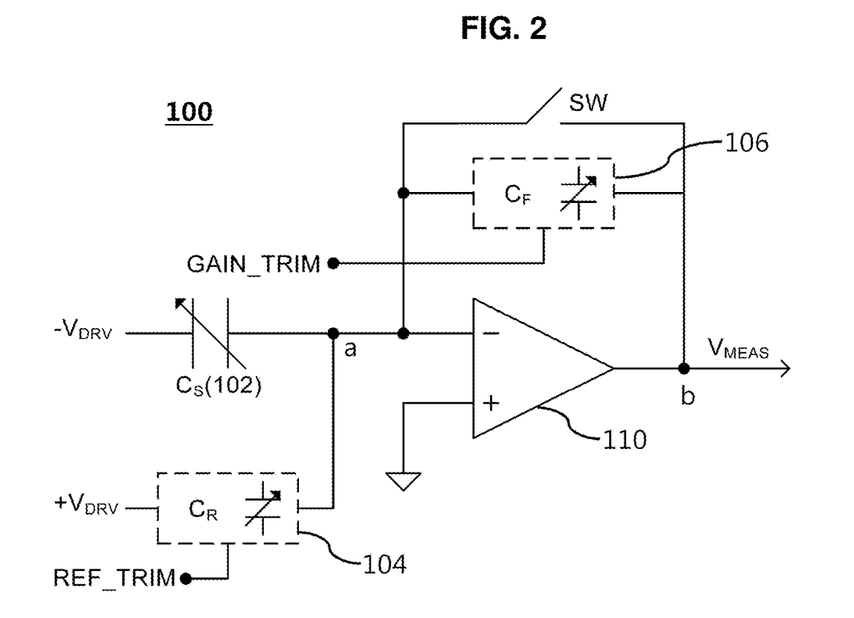
FIG. 2 is a diagram illustrating an example of a circuit of a capacitor type humidity sensor.

FIG. 2 is a diagram illustrating an example of a circuit of a capacitor type humidity sensor. Referring to the example of FIG. 2, the capacitor type humidity sensor 100 receives drive voltage from negative (−) drive voltage terminal (−$V_{DRV}$) and positive (+) drive voltage terminal (+$V_{DRV}$). The drive voltage is in a toggle state and is inputted such that it does not overlap each other. A sensing capacitor ($C_S$) 102 is connected to negative (−) drive voltage terminal (−$V_{DRV}$). A reference capacitor ($C_R$) 104 is connected between an output node (a) of the sensing capacitor ($C_S$) 102 and + drive voltage terminal (+$V_{DRV}$).

The output node (a) is connected to an inverting terminal (−) of an operational amplifier 110. A non-inverting terminal (+) of the operational amplifier 110 is AC grounded. AC ground has about half the voltage level of the input drive voltage.

A feedback capacitor ($C_F$) 106 having a certain capacitance and a reset switch (sw) are connected to the inverting terminal (−) of the operational amplifier 110 and the output terminal (b). The reset switch (sw) is used to reset a value of the feedback capacitor ($C_F$) 106, and the drive voltage is inputted.

Values of the reference capacitor ($C_R$) 104 and the feedback capacitor ($C_F$) 106 are adjustable by a reference trimming signal (REF_TRIM) and a gain trimming signal (GAIN_TRIM). The values of the reference capacitor ($C_R$) 104 and the feedback capacitor ($C_F$) 106 maybe selectively adjusted based on output voltage ($V_{MEAS}$).

In order to perform the trimming, the reference capacitor ($C_R$) 104 and the feedback capacitor ($C_F$) 106 of the capacitor type humidity sensor 100 are realized as the MIM capacitor or the PIP capacitor. The MIM (metal insulator metal) capacitor or the PIP (polysilicon insulator polysilicon) capacitor provides independent characteristics on bias, unlike that of an MOS (Metal Oxide Silicon) capacitor or a junction capacitor.

Figure 3:
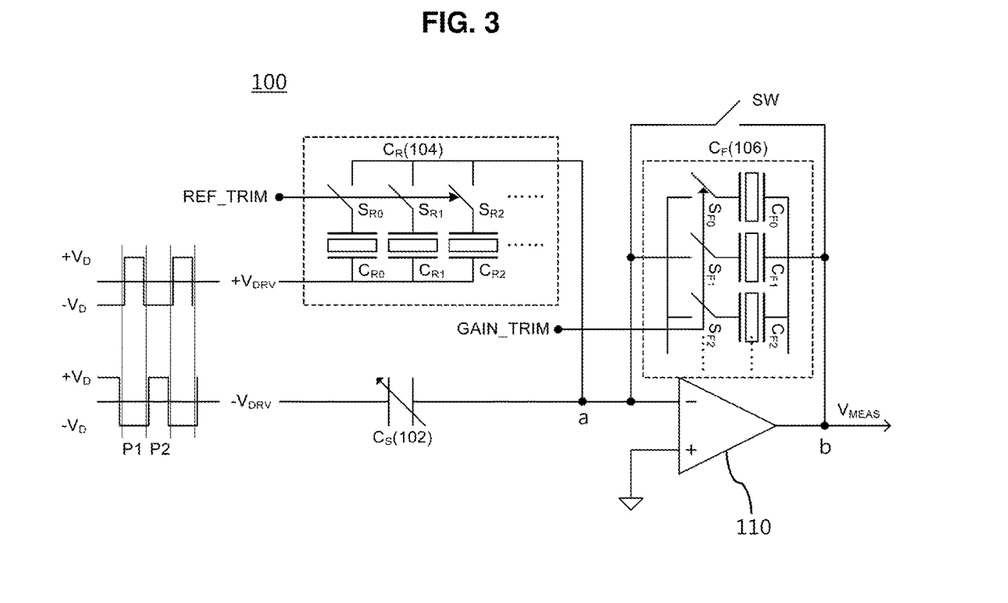
FIG. 3 is a diagram illustrating an example of the capacitor type humidity sensor of FIG. 2.

FIG. 3 is a diagram illustrating an example of the capacitor type humidity sensor of FIG. 2. In the capacitor type humidity sensor of FIG. 3, the MIM capacitor or the PIP capacitor are applied to the reference capacitor ($C_R$) 104 and the feedback capacitor ($C_F$) 106.

Referring to the example of FIG. 3, the reference capacitor ($C_R$) 104 is connected between positive (+) drive voltage terminal (+$V_{DRV}$) and output node (a) of the sensing capacitor ($C_S$) 102.

One or more individual reference capacitors ($C_{R0}$, $C_{R1}$, $C_{R2}$ . . . ) as an MIM capacitor or a PIP capacitor are connected in array structure to form the reference capacitor ($C_R$) 104. Switches ($S_{R0}$, $S_{R1}$, $S_{R2}$ . . . ) are connected to individual reference capacitors ($C_{R0}$, $C_{R1}$, $C_{R2}$ . . . ). A reference trimming signal (REF_TRIM) is selectively applied as the switches ($S_{R0}$, $S_{R1}$, $S_{R2}$ . . . ) are turned on.

The individual reference capacitors ($C_{R0}$, $C_{R1}$, $C_{R2}$ . . . ) have the same value or have a power of 2. For example, the individual reference capacitors ($C_{R0}$, $C_{R1}$, $C_{R2}$ . . . ) may each have 1 pF. In another example, $C_{R0}$, $C_{R1}$, $C_{R2}$, and $C_{R3}$, may be set as 1 pF, 2 pF, 4 pF, and 8 pF, respectively. The individual reference capacitors ($C_{R0}$) $C_{R1}$, $C_{R2}$ . . . ) are allowed for a fine trimming as their number is large. The number of individual reference capacitors ($C_{R0}$, $C_{R1}$, $C_{R2}$ . . . ) may be determined by collectively considering a size and performance of the capacitor type humidity sensor 100.

When the reference capacitor ($C_R$) 104 is an MIM capacitor or a PIP capacitor manufactured by the typical semiconductor process, it is possible to manufacture a smaller capacitor type humidity sensor 100. For example, a capacitance per unit area of the typical MIM capacitor ranges from 1 fF/u$^2$ to 4 fF/u$^2$, a capacitance per unit area of the sensing capacitor approximately ranges from 0.001 fF/u$^2$ to 0.1 fF/u$^2$. The capacitance per an area of the MIM capacitor is higher.

The feedback capacitor ($C_F$) 106 has one or more individual feedback capacitors ($C_{F0}$, $C_{F1}$, $C_{F2}$ . . . ) as an MIM capacitor or a PIP capacitor arranged in array structure. Switches ($S_{F0}$, $S_{F1}$, $S_{F2}$ . . . ) are connected to individual feedback capacitors ($C_{F0}$, $C_{F1}$, $C_{F2}$ . . . ). A gain trimming signal (GAIN_TRIM) is applied through the switches ($S_{F0}$, $S_{F1}$, $S_{F2}$ . . . ).

When the feedback capacitor ($C_F$) 106 is realized as an MIM capacitor or PIP capacitor as discussed above, it is possible to adjust a gain and to manufacture a humidity sensor more precisely.

The present examples discuss the reference capacitor ($C_R$) 104 and the feedback capacitor ($C_F$) 106 embodied as the MIM capacitor or the PIP capacitor to enable trimming. Trimming values of a reference capacitor ($C_R$) 104 and a feedback capacitor ($C_F$) 106 are discussed below.

As illustrated in the example of FIG. 3, positive (+) drive voltage terminal (+$V_{DRV}$) and negative (−) drive voltage terminal (−$V_{DRV}$) receive a drive input voltage in a toggle state during a certain cycle. An input waveform is applied to positive (+) drive voltage terminal (+$V_{DRV}$) and negative (−) drive voltage terminal (−$V_{DRV}$) at ±$V_D$ level. The moment at which voltages inputted to negative (−) drive voltage terminal (−$V_{DRV}$) and positive (+) drive voltage terminal (+$V_{DRV}$) are transient and is configured to not intersect each other. A duty cycle of a voltage −$V_D$ inputted to negative (−) drive voltage terminal (−$V_{DRV}$) at P1 section is longer than the duty cycle of a voltage +$V_D$ inputted to positive (+) drive voltage terminal (+$V_{DRV}$) at P2 section. A duty cycle of the voltage +$V_D$ inputted to positive (+) drive voltage terminal (+$V_{DRV}$) at P1 section is shorter than the duty cycle of the voltage −$V_D$ inputted to negative (−) drive voltage terminal (−$V_{DRV}$) at P2 section. This configuration is intended to remove a time point at which negative (−) drive voltage terminal (−$V_{DRV}$) and positive (+) drive voltage terminal (+$V_{DRV}$) are simultaneously turned on or off. The duration of P1 section is the same as that of P2 section.

When a drive voltage is applied in this manner, a charge proportional to capacitance generated between each electrode of the sensing capacitor ($C_S$) 102 and the reference capacitor ($C_R$) 104 is accumulated to the feedback capacitor ($C_F$) 106. Voltage corresponding to the accumulated charge is outputted as output voltage ($V_{MEAS}$) through output terminal (b).

Here, the output voltage ($V_{MEAS}$) is outputted differently in accordance with a process deviation or the like. If capacitor value of the sensing capacitor ($C_S$) 102 has deviation of ±$\Delta C_O$ and ±$\Delta C_{Humidity}$ due to the process deviation, output voltage ($V_{MEAS}$) can be expressed by function of relative humidity (RH) as shown in Equation 1 below:

$$V_{MEAS}(RH) = V_D \cdot \frac{C_S - C_R}{C_F} \qquad \text{Equation 1}$$

$$= V_D \cdot \frac{C_0 \pm \Delta C_0 + (C_{Humidity} \pm \Delta C_{Humidity}) \cdot RH - C_R}{C_F}$$

$C_O$ represents an initial capacitance irrespective of the humidity, and $C_{Humidity}$ represents capacitance as a changing component due to the relative humidity (RH).

Figure 4:
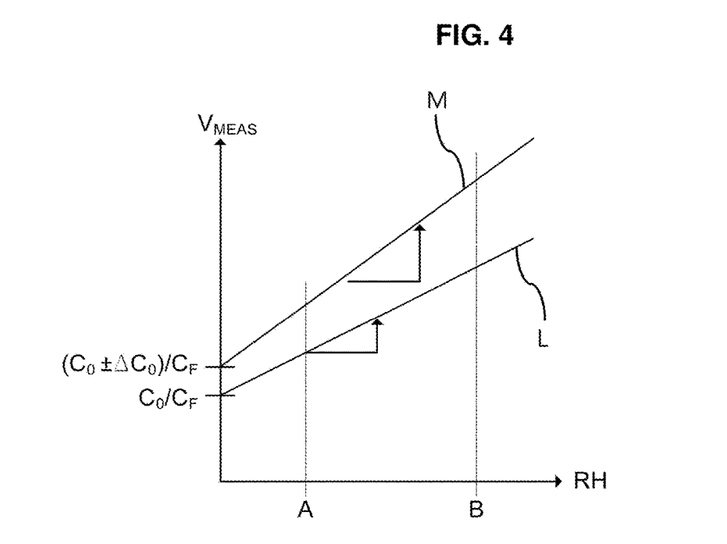
FIG. 4 is a diagram illustrating an example of a slope variation in accordance with an output voltage and a relative humidity of the capacitor type humidity sensor of FIG. 3.

Based on Equation 1, a slope value before the trimming and an ideal slope value are compared as illustrated in the example of FIG. 4.

Referring to FIG. 4, a slope value ($C_{Humidity}/C_F$) in an ideal state where there are no offsets of the sensing capacitor ($C_S$) 102 is expressed by the reference numeral 'L', and a slope value ($C_{Humidity} \pm \Delta C_{Humidity}/C_F$) where there are offsets of the sensing capacitor ($C_S$) 102 due to the process deviation is expressed by the reference numeral 'M'. The slope values are different from each other.

Figure 5:
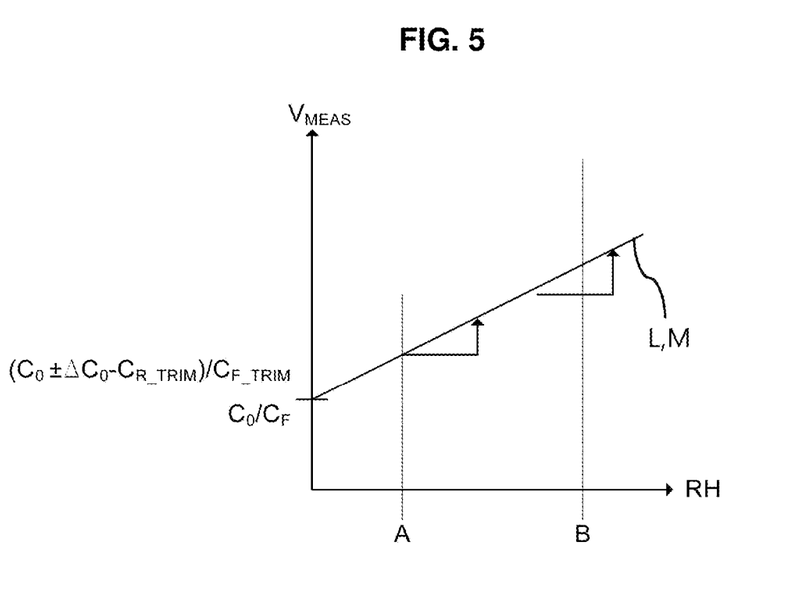
FIG. 5 is a diagram illustrating an example of a slope characteristic after performing trimming with respect to the capacitor type humidity sensor of FIG. 3.

According to the present example, such offsets can be reduced or removed based on the trimming with respect to the reference capacitor ($C_R$) 104. As illustrated in the example of FIG. 5, a slope that is substantially equal to or similar with the ideal slope value ($C_{Humidity}/C_F$) is obtained. This process is achieved by obtaining a trimming value of the reference capacitor ($C_R$) 104. The obtaining of the ideal value is now described with reference to the straight lines 'L' and 'M,' which are of different slopes.

In FIG. 4, the results of subtracting a point 'A' voltage from a point 'B' voltage on M is expressed according to equation 2 below.

$$V_{MEAS\_TRIM}(B) - V_{MEAS\_TRIM}(A) = \qquad \text{Equation 2}$$

$$V_D \cdot \frac{(C_{Humidity} \pm \Delta C_{Humidity}) \cdot (B - A)}{C_{F\_TRIM}}$$

The results of subtracting a point 'A' voltage from a point 'B' voltage on L is expressed according to equation 3 below.

$$V_{MEAS\_IDEAL}(B) - V_{MEAS\_IDEAL}(A) = V_D \cdot \frac{(C_{Humidity}) \cdot (B-A)}{C_F} \quad \text{Equation 3}$$

Meanwhile, the slope M according to the trimming results is required to be the same as the slope L. Therefore, to satisfy the Equation 2 and the Equation 3, the same conditions as those of Equation 4 below are required.

$$V_{MEAS_{TRIM}}(B) - V_{MEAS_{TRIM}}(A) = \quad \text{Equation 4}$$
$$V_{MEAS_{IDEAL}}(B) - V_{MEAS_{IDEAL}}(A)$$

Therefore, using the Equations 2 to 4, a trimming value of the feedback capacitor ($C_F$) 106 is obtained according to Equation 5 below.

$$C_{F\_TRIM} = C_F \cdot \frac{v_{MEAS}(B) - v_{MEAS}(A)}{V_{MEAS_{IDEAL}}(B) - V_{MEAS_{IDEAL}}(A)} \quad \text{Equation 5}$$

If the trimming value of the feedback capacitor ($C_F$) 106 is obtained, a trimming value of the reference capacitor ($C_R$) 104 is obtained. Such calculation is expressed according to Equation 6 below.

$$C_{R_{TRIM}} = C_R + \frac{V_{MEAS}(A) \cdot C_F}{V_D} - V_{MEAS_{IDEAL}}(A) \cdot C_{F_{TRIM}} \quad \text{Equation 6}$$

The process of obtaining a trimming value of the feedback capacitor ($C_F$) 106 and a trimming value of the reference capacitor ($C_R$) 104 is described above.

A corresponding switch among switches $S_{R0}$, $S_{R1}$, $S_{R2}$ ... and switches $S_{F0}$, $S_{F1}$, $S_{F2}$ ... is turned so that the individual reference capacitor or the individual feedback capacitor close to the obtained trimming value may be connected. Thus, offsets of the sensing capacitor ($C_S$) 102 are reduced or removed.

Figure 6:
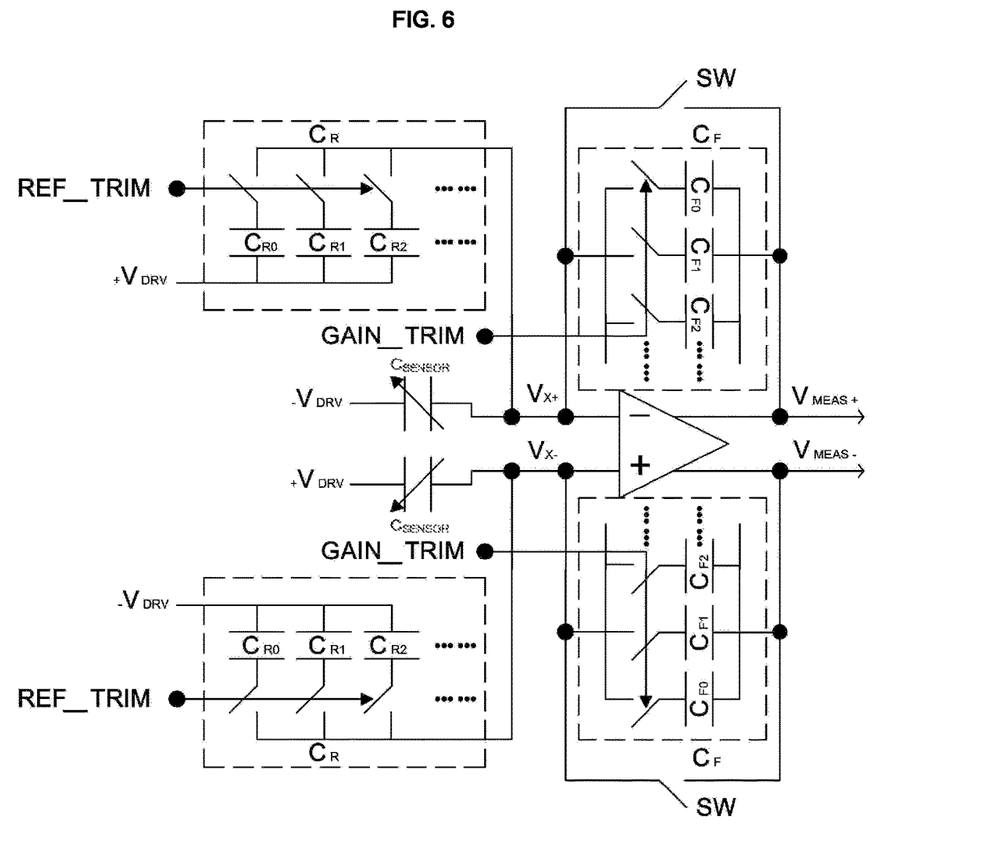
FIG. 6 is a diagram illustrating an example of a circuit of a capacitor type humidity sensor.

FIG. 6 is a diagram illustrating an example of a circuit of a capacitor type humidity sensor. Referring to the example of FIG. 6, an MIM capacitor or a PIP capacitor is provided in an array structure and in mirror structure to enable trimming with respect to an inverting terminal (−) and a non-inverting terminal (+) of the operational amplifier 110.

The capacitor type humidity sensor illustrated in the examples of FIGS. 2 and 3 is such that the non-inverting terminal (+) of the operational amplifier is AC grounded. However the non-inverting terminal (+) may be shaken or the noise may be contained in some occasions. Consequently, effects obtained from the trimming may be offset.

On the other hand, referring to the example of FIG. 6, a reference capacitor ($C_R$) and a feedback capacitor ($C_F$) which are connected to the inverting terminal (−) and the non-inverting terminal (+) of the operational amplifier, respectively, are an MIM capacitor or a PIP capacitor in an array form. Here, the output is a potential difference between positive (+) output voltage ($V_{MEAS+}$) and negative (−) output voltage ($V_{MEAS-}$). Thus, regardless of the state of the AC grounded non-inverting terminal (+), offset values of the sensing capacitor ($C_S$) may be controlled.

As discussed so far, the present examples are configured to have the MIM capacitor or the PIP capacitor as a reference capacitor ($C_R$) or a feedback capacitor ($C_F$) of a capacitor type humidity sensor to enable trimming.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A capacitor type humidity sensor comprising:
    a sensing capacitor connected between a negative drive voltage terminal and an inverting terminal of an operational amplifier; and
    a reference capacitor connected between a positive drive voltage terminal and an output node of the sensing capacitor,
    wherein the reference capacitor is configured to be trimmed by a trimming value of the reference capacitor so as to reduce or remove offsets of the sensing capacitor, and determination of the trimming value of the reference capacitor is based on a trimming value of a feedback capacitor.

2. The capacitor type humidity sensor of claim 1, wherein the reference capacitor comprises one or more MIM (metal insulator metal) capacitor or PIP (polysilicon insulator polysilicon) capacitor arranged in an array.

3. The capacitor type humidity sensor of claim 2, wherein the each MIM capacitor or PIP capacitor of the array have a same first value or have a value that is the first value times a power of 2.

4. The capacitor type humidity sensor of claim 2, further comprising a switch connected to the each MIM capacitor or the PIP capacitor of the array, and the switch being configured to selectively apply a reference trimming signal.

5. The capacitor type humidity sensor of claim 2, wherein a number of the MIM capacitor or a number of the PIP capacitor of the array is determined based on a size and performance of the capacitor type humidity sensor.

6. The capacitor type humidity sensor of claim 1, wherein the feedback capacitor is connected between the inverting terminal of the operational amplifier and the output terminal of the operational amplifier, wherein the feedback capacitor comprises one or more MIM (metal insulator metal) capacitor or PIP (polysilicon insulator polysilicon) capacitor configured in an array structure.

7. The capacitor type humidity sensor of claim 6, further comprising a reset switch connected between the inverting terminal of the operational amplifier and the output terminal of the operational amplifier and the reset switch being configured to reset the feedback capacitor.

8. A capacitor type humidity sensor comprising:
    a sensing capacitor connected between a negative drive voltage terminal and an inverting terminal of an operational amplifier;

a reference capacitor connected between a positive drive voltage terminal and an output node of the sensing capacitor; and a feedback capacitor connected between a non-inverting terminal of the operational amplifier and an output terminal of the operational amplifier, wherein the reference capacitor is configured to be trimmed by a trimming value of the reference capacitor so as to reduce or remove offsets of the sensing capacitor, wherein the feedback capacitor comprises one or more MIM (metal insulator metal) capacitor or PIP (polysilicon insulator polysilicon) capacitor configured in an array structure, and wherein a gain of the feedback capacitor is adjusted by applying a gain trimming signal to the feedback capacitor.

9. The capacitor type humidity sensor of claim 8, wherein the non-inverting terminal of the operational amplifier is connected to an AC ground.

10. The capacitor type humidity sensor of claim 9, wherein a duty cycle of a voltage inputted at the positive drive voltage terminal is longer than a duty cycle of a voltage inputted at the negative drive voltage terminal.

11. A capacitor type humidity sensor comprising:
a first reference capacitor connected to an inverting terminal of an operational amplifier;
a second reference capacitor connected to a non-inverting terminal of the operational amplifier;
sensing capacitors respectively connected between the inverting terminal of the operational amplifier and a negative drive voltage terminal and between the non-inverting terminal of the operational amplifier and a positive drive voltage terminal; and
a first feedback capacitor connected between the non-inverting terminal of the operational amplifier and an output terminal of the operational amplifier,
wherein each of the first and second reference capacitors comprises MIM (metal insulator metal) capacitors or PIP (polysilicon insulator polysilicon) capacitors arranged in an array structure and structures of the first and second reference capacitors mirror each other, and
wherein switches are connected to individual respective ones of the MIM capacitors or PIP capacitors.

12. The capacitor type humidity sensor of claim 11, further comprising:
a second feedback capacitor connected between the inverting terminal and the output terminal of the operational amplifier,
wherein each of the first and second feedback capacitors comprises one or more MIM capacitor or PIP capacitor configured in an array structure.

13. The capacitor type humidity sensor of claim 12, wherein a gain is adjusted by applying a gain trimming signal to the first and second feedback capacitors.

14. The capacitor type humidity sensor of claim 11, wherein the first and second reference capacitors are configured to be trimmed by a trimming value so as to reduce or remove offsets of the sensing capacitors.

15. The capacitor type humidity sensor of claim 11, wherein a reference trimming signal selectively controls the switches.

* * * * *